(12) United States Patent
Hoernig et al.

(10) Patent No.: US 10,765,393 B2
(45) Date of Patent: Sep. 8, 2020

(54) METHOD AND IMAGE DATA SYSTEM FOR GENERATING A COMBINED CONTRAST MEDIUM AND BLOOD VESSEL REPRESENTATION OF BREAST TISSUE TO BE EXAMINED, COMPUTER PROGRAM PRODUCT AND COMPUTER-READABLE MEDIUM

(71) Applicant: SIEMENS HEALTHCARE GMBH, Erlangen (DE)

(72) Inventors: Mathias Hoernig, Erlangen (DE); Michael Kelm, Erlangen (DE); Thomas Mertelmeier, Erlangen (DE); Wei Wei, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 582 days.

(21) Appl. No.: 15/467,132

(22) Filed: Mar. 23, 2017

(65) Prior Publication Data

US 2017/0273653 A1    Sep. 28, 2017

(30) Foreign Application Priority Data

Mar. 23, 2016    (DE) .................. 10 2016 204 828

(51) Int. Cl.
*A61B 6/00* (2006.01)
*A61B 6/02* (2006.01)
*A61B 6/03* (2006.01)

(52) U.S. Cl.
CPC .......... *A61B 6/5235* (2013.01); *A61B 6/025* (2013.01); *A61B 6/03* (2013.01); *A61B 6/481* (2013.01);

(Continued)

(58) Field of Classification Search
CPC ....... A61B 6/5235; A61B 6/504; A61B 6/502; A61B 6/025; A61B 6/481; A61B 6/03;
(Continued)

(56) References Cited

U.S. PATENT DOCUMENTS 4,324,187 A     4/1982   Sambo
4,662,379 A  *  5/1987   Macovski .............. A61B 6/025
                                                     348/E5.089

(Continued)

FOREIGN PATENT DOCUMENTS

DE        4410970 C1      7/1995
DE        10122875 C1     2/2003
(Continued)

OTHER PUBLICATIONS

R Karunamuni, et al., "Search for novel contrast materials in dual-energy x-ray breast imaging using theoretical modeling of contrast-to-noise ratio", 2014, pp. 4311-4324, IOP Sience.

(Continued)

*Primary Examiner* — Sanjay Cattungal
(74) *Attorney, Agent, or Firm* — Laurence Greenberg; Werner Stemer; Ralph Locher

(57) ABSTRACT

A method for generating a combined contrast medium and blood vessel representation of contrast-enhanced image data of breast tissue to be examined includes capturing first and second contrast-medium-influenced x-ray projection measurement data of the breast tissue with respective differing first and second x-ray energies. First and second image data sets are reconstructed based respectively on the first and second measurement data. A dual-energy image data set is ascertained based on the first and the second image data sets. A blood vessel image is ascertained based on at least one image data set. A blood vessel image is represented together with the dual-energy image data set in a combined contrast (Continued)

medium and blood vessel representation. An image data generating system is also provided.

16 Claims, 5 Drawing Sheets

(52) U.S. Cl.
CPC .............. *A61B 6/482* (2013.01); *A61B 6/502* (2013.01); *A61B 6/504* (2013.01)

(58) Field of Classification Search
CPC ..... A61B 6/482; A61B 6/0414; A61B 6/5217; A61B 6/405; G16H 50/30
See application file for complete search history.

(56) References Cited

U.S. PATENT DOCUMENTS

| | | | |
|---|---|---|---|
| 6,650,724 B2 | 11/2003 | Strobel | |
| 6,950,493 B2* | 9/2005 | Besson | A61B 6/032 378/16 |
| 7,218,702 B2* | 5/2007 | Mistretta | A61B 6/025 378/21 |
| 8,356,557 B2 | 1/2013 | Schneider | |
| 8,594,274 B2* | 11/2013 | Hoernig | A61B 6/025 378/22 |
| 2004/0114706 A1* | 6/2004 | Ikeda | A61B 6/481 378/4 |
| 2006/0067473 A1* | 3/2006 | Eberhard | A61B 6/5288 378/98.9 |
| 2008/0130824 A1* | 6/2008 | Fujisawa | A61B 6/5235 378/4 |
| 2009/0022265 A1* | 1/2009 | Takase | A61B 6/469 378/8 |
| 2009/0028289 A1* | 1/2009 | Tsuyuki | A61B 6/465 378/8 |
| 2009/0028405 A1* | 1/2009 | Degani | G06T 7/0012 382/131 |
| 2009/0028409 A1* | 1/2009 | Tsukagoshi | A61B 6/507 382/131 |
| 2009/0092225 A1* | 4/2009 | Boese | A61B 6/027 378/19 |
| 2009/0129536 A1* | 5/2009 | Ichihara | A61B 6/504 378/4 |
| 2009/0304253 A1* | 12/2009 | Puong | G06T 5/50 382/131 |
| 2010/0091943 A1* | 4/2010 | Kang | G01N 23/04 378/4 |
| 2013/0163719 A1* | 6/2013 | Tsujii | A61B 6/545 378/41 |
| 2014/0072096 A1 | 3/2014 | Hoernig | |
| 2016/0007943 A1 | 1/2016 | Hoernig | |
| 2016/0022233 A1 | 1/2016 | Fieselmann et al. | |

FOREIGN PATENT DOCUMENTS

| | | |
|---|---|---|
| DE | 102010041920 A1 | 4/2012 |
| DE | 102012215997 A1 | 3/2014 |
| DE | 102014213464 A1 | 1/2016 |
| DE | 102014214772 A1 | 1/2016 |
| RU | 2376181 C2 | 12/2009 |
| WO | 2010113045 A2 | 10/2010 |

OTHER PUBLICATIONS

Marius Staring, et al., "Pulmonary Vessel Segmentation using Vessel Enhancement Filters", pp. 1-8.
Alejandro F. Frangi, et al., "Multiscale vessel enhancement filtering", 1998, pp. 130-137, vol. 1496, Springer Verlag, Berlin, Germany.

* cited by examiner

METHOD AND IMAGE DATA SYSTEM FOR GENERATING A COMBINED CONTRAST MEDIUM AND BLOOD VESSEL REPRESENTATION OF BREAST TISSUE TO BE EXAMINED, COMPUTER PROGRAM PRODUCT AND COMPUTER-READABLE MEDIUM

CROSS-REFERENCE TO RELATED APPLICATION

This application claims the priority, under 35 U.S.C. § 119, of German Patent Application DE 10 2016 204 828.7, filed Mar. 23, 2016; the prior application is herewith incorporated by reference in its entirety.

BACKGROUND OF THE INVENTION

Field of the Invention

The invention relates to a method for generating a combined contrast medium and blood vessel representation of breast tissue to be examined. In the method according to the invention for generating a combined contrast medium and blood vessel representation of breast tissue to be examined, first contrast-medium-influenced x-ray projection measurement data of the breast tissue to be examined are captured with a first x-ray energy and second contrast-medium-influenced x-ray projection measurement data are captured with a second x-ray energy which differs from the first x-ray energy. Projection measurement data, which are contrast-medium-influenced or contrast-medium-supported, are understood to mean projection measurement data that were recorded after a contrast agent was administered and transported into the examination region. Based on the captured first x-ray projection measurement data, a first image data set is reconstructed, and based on the captured second x-ray projection measurement data, a second image data set of the breast tissue to be examined is reconstructed. An image reconstruction within that context is understood to mean ascertainment of an image representation based on the captured measurement data. In the case of captured two-dimensional measurement data, that can mean, for example, simple preparation, in particular suppression or correction of available measurement data, which already contain an image representation. However, in the case of a recording of projection measurement data from various directions, an image reconstruction can also include the reconstruction of a three-dimensional image. Subsequently, a dual energy image data set is ascertained on the basis of the first and the second image data set. The invention furthermore relates to an image data generating system.

Mammography continues to play an important role for the early detection of breast carcinoma. In classical mammograms, an x-ray recording of the female breast is made. The x-rays used in that case are soft radiation with an energy of approximately 25 to 35 keV. In order to detect the x-rays, direct digital detectors and indirect digital detectors are used to capture the emitted x-rays. Direct digital detectors convert the x-rays directly into an electrical signal. Indirect digital detectors, on the other hand, first convert the x-rays into visible light, which is subsequently converted into an electrical signal. The x-ray recordings are viewed on a special mammography diagnostic workstation, which includes one or two grayscale monitors with which the x-ray images are represented in the form of images. A configuration relating to two-dimensional mammography is shown in FIG. 1.

In order to be able to eliminate tissue structures, which possibly cover lesions, from the image-based representation in contrast-enhanced dual energy mammography (CEDEM), typically a high-energy recording followed by a low-energy mammography recording is carried out while maintaining the breast compression, after the contrast medium has previously been administered. Registration and a weighted subtraction is then followed by the creation of a recombined result image, in which substantially regions in which the contrast medium has accumulated are represented with particularly good visibility. In other words, the different x-ray energies are selected in such a way that the value of the lower energy is near the energy value of the absorption edge of the contrast medium used for x-rays, and the value of the high energy is far above the energy value of the absorption edge of the contrast medium used for x-rays. By way of example, the K-absorption edge for x-rays of the contrast medium iodine, which is also referred to for short as x-ray absorption edge below, is 33.17 keV. An energy value selection of this type for the x-rays for the different recordings results in the structures which are penetrated by the contrast medium, such as for example lesions, in the breast tissue to be captured more clearly when imaging with x-rays with lower energy than when imaging with x-rays with higher energy. If a difference image is created from both images, the result is an image of the lesions without interfering or covering background structures or tissue structures, which simplifies diagnosing the lesions.

In traditional two-dimensional mammography there is a problem which is that due to the superposition of different tissue structures, pathological changes in the tissue are often covered and consequently they are not identified. Attempts have been made to compensate for that problem by recording the breast from two different angles, "craniocaudal" and "mediolateral oblique," i.e. once perpendicular and once at a 45° angle with respect thereto.

3D breast tomosynthesis offers an imaging method in which the breast is recorded from many different angles. For example, recordings are taken at angles from 15 to 50 degrees. Overall, for example, between 9 and 25 recordings from different angles are recorded with a low dose and high acceleration voltage, in such a way that the total dose corresponds approximately to that of a classical two-dimensional mammography recording. Images for individual layers of the breast tissue are calculated from the captured projection data. The method of filtered back projection is used, for example, for the reconstruction of a three-dimensional image of a region to be examined from the captured projection data. The resulting three-dimensional image can be viewed in layer-wise fashion for diagnostics purposes. Since layers above and below the layer that is respectively selected for view can be removed during the diagnosis, tissue changes can be identified more easily. A system for three-dimensional imaging of breast tissue with the aid of tomosynthesis is illustrated in FIG. 2.

Calculating a recombined dual-energy mammogram from 3D breast tomosynthesis (CEDET) is known from German Patent Application DE 10 2012 215 997 A1, corresponding to U.S. Publication US 2014/0072096. In that method, a high-energy tomosynthesis recording and a low-energy tomosynthesis recording are taken, and a difference image is ascertained from the two recordings.

German Patent Application DE 10 2014 213 464 A1, corresponding to U.S. Publication US 2016/0007943, describes a method for combined dual energy mammography and tomosynthesis imaging. The image recordings are taken with identical position and compression of the breasts.

German Patent Application DE 10 2012 215 997 A1, corresponding to U.S. Publication US 2014/0072096, describes a method, in which both three-dimensional and two-dimensional representations of breast tissue are generated on the basis of projection image sequences.

German Patent Application DE 10 2014 214 772 A1, corresponding to U.S. Publication US 2016/0022233, describes a method for generating a blood vessel representation, wherein blood vessels are selectively represented in dependence on an area which carries the flow and a contrast medium arrival time.

German Patent DE 101 22 875 C1, corresponding to U.S. Pat. No. 6,650,724, describes a 3D angio volume reconstruction method, wherein reconstruction of a vessel tree is carried out on the basis of a fill volume data set and the representation generated in the process is added to a mask image volume data set.

German Patent Application DE 10 2010 041 920 A1, corresponding to U.S. Pat. No. 8,594,274, describes the representation of a contrast medium concentration by a combination of two-dimensional contrast-medium-supported image recordings, which were obtained on the basis of a non-temporary subtraction, and three-dimensional contrast-medium-supported image recordings, which were obtained from a temporary subtraction.

A sign of the presence of tissue changes are blood vessel structures and their manifestation in a region to be examined. These vessel structures, however, can no longer be detected in the described contrast-enhanced image representations. That is to say that in such imaging methods of the breasts, vessel representation is no longer possible, because the vessel image data are no longer present in the image representation in the case of a subtraction of the high-energy recordings and the low-energy recordings.

SUMMARY OF THE INVENTION

It is accordingly an object of the invention to provide a method and an image data system for generating a combined contrast medium and blood vessel representation of breast tissue to be examined, a computer program product and a computer-readable medium, which overcome the hereinafore-mentioned disadvantages of the heretofore-known devices and methods of this general type and which provide an information content that is increased, as compared to a contrast image representation.

With the foregoing and other objects in view there is provided, in accordance with the invention, a method for generating a combined contrast medium and blood vessel representation of breast tissue to be examined. The method includes the steps of:
  capturing first contrast-medium-influenced x-ray projection measurement data with a first x-ray energy and second contrast-medium-influenced x-ray projection measurement data with a second x-ray energy that differs from the first x-ray energy,
  reconstructing a first image data set on the basis of the captured first x-ray projection measurement data and a second image data set on the basis of the captured second x-ray projection measurement data,
  ascertaining a dual-energy image data set on the basis of the first and the second image data sets,
  ascertaining a blood vessel image on the basis of at least one of the two image data sets, and
  representing the blood vessel image together with the dual-energy image data set in a combined contrast medium and blood vessel representation.

With the objects of the invention in view, there is concomitantly provided an image data generating system, including:
  a projection data capturing unit for capturing first contrast-medium-influenced x-ray projection measurement data with a first x-ray energy and second contrast-medium-influenced x-ray projection measurement data with a second x-ray energy that differs from the first x-ray energy,
  an image data generating unit for reconstructing a first image data set of the breast tissue to be examined on the basis of the captured first x-ray projection measurement data and a second image data set of the breast tissue to be examined on the basis of the captured second x-ray projection measurement data, and
  an evaluation unit, including:
    a dual-energy image ascertainment unit, which is configured to ascertain a dual-energy image data set on the basis of the first and the second image data sets,
    a blood vessel image ascertainment unit, which is configured to ascertain a blood vessel image on the basis of at least one of the two image data sets, and
    a combination image ascertainment unit, which is configured to ascertain a combined contrast medium and blood vessel representation of the blood vessel image and of the dual-energy image data set.

According to the invention, in addition to generating a contrast image representation, also referred to as a dual-energy image data set, a blood vessel image is ascertained on the basis of at least one of the two image data sets which are used for generating the dual-energy image data set. The blood vessel image is ultimately represented together with the dual-energy image data set in a combined contrast medium and blood vessel representation.

The representation form according to the invention has the advantage that it contains image regions as an indication of any angiogenesis and can thus be used as an indicator of a tumor. In addition, the functional and morphological information in the combined representation provides a diagnostic multiple value. Furthermore, the diagnosis is significantly facilitated due to the merged representation. As a result, time for the diagnosis and consequently also costs are saved.

The image data generating system according to the invention has a projection measurement data capturing unit for capturing first contrast-medium-influenced x-ray projection measurement data of the breast tissue to be examined with a first x-ray energy and second contrast-medium-influenced x-ray projection measurement data with a second x-ray energy that differs from the first x-ray energy.

Where x-ray energy is mentioned below, it generally refers to the average energy of the x-ray energy spectrum of the emitted x-rays. For example, for an x-ray tube voltage of 80 kV, the average energy of the x-ray spectrum is approximately 55 keV. The x-ray energy spectrum refers to the energy distribution of the x-ray quanta generated by an x-ray tube. Typically, x-rays emitted by an x-ray source do not only have a discrete energy, but an entire spectrum of radiation with different energy values. In addition to that average value of the energy distribution, an energy value e*U can be assigned to the emitted x-rays, which value defines a minimum wavelength or maximum energy of the x-ray quanta of the x-rays. (This value in this concrete example would be 80 keV and is intended to be mentioned in this case only for better differentiation.) Also part of the image data generating system according to the invention is an Image data generating unit for reconstructing a first image data set of the breast tissue to be examined on the basis of the captured first x-ray projection measurement data and a second image data set of the breast tissue to be examined on the basis of the captured second x-ray projection measurement data. In addition, the image data generating system according to the invention includes an evaluation unit, which has, among others, a dual-energy image ascertainment unit, which is configured to ascertain a dual-energy image data set on the basis of the first and the second image data set. A dual-energy image data set in this context is intended to include a contrast image representation, in which the regions of the image representation that are not affected by the contrast medium are eliminated or at least reduced in terms of their intensity. The image data generating system according to the invention additionally includes a blood vessel image ascertainment unit, which is configured to ascertain a blood vessel image on the basis of at least one of the two image data sets. A blood vessel image in this context is intended to be an image representation in which the blood vessels that are present in a region to be examined are detectable. Moreover, the image data generating system according to the invention includes a combination image ascertainment unit, which is configured to ascertain a combined contrast medium and blood vessel representation of the blood vessel image and of the dual-energy image data set. A combined representation is understood to mean a representation that includes the information of both types of representation, that is to say both of the contrast-medium-influenced representation and of the blood vessel representation.

The central components of the image data generating system according to the invention can be realized predominantly in the form of software components. This relates in particular to parts of the projection measurement data-capturing unit, the image data generating unit and the evaluation unit and the units included thereby, such as the dual-energy image ascertainment unit, the blood vessel image ascertainment unit and the combination image ascertainment unit. In principle, those components can also be realized in part, especially in the case of particularly fast calculations, in the form of software-supported hardware, for example FPGAs or the like. The required interfaces can also be implemented as software interfaces, for example if only a transfer of data from other software components is required. However, they can also be implemented in the form of interfaces which are constructed in terms of hardware, and which are driven by suitable software.

A largely software-based realization has the advantage that image data generating systems that are already in use can be retrofitted simply by way of a software update so that they operate in the manner according to the invention. To this extent, the object is achieved by way of a corresponding computer program product with a computer program, which may be loaded directly into a storage device of an image data generating system according to the invention, with control or program sections for carrying out all of the steps of the method according to the invention if the computer program in the image data generating system is executed.

In addition to the computer program, such a computer program product can also include additional components, such as for example documentation and/or additional components, also hardware components, such as for example hardware keys (dongles, etc.) for utilizing the software.

For transport to the storage device of the image data generating system and/or for storing at the image data generating system, a computer readable medium, such as for example a memory stick, a hard drive or another transportable or fixedly installed data carrier can be used, on which the control or program sections of the computer program which are readable and executable by a computer unit of the image data generating system are stored. The computer unit can have, for example, one or more cooperating microprocessors or the like for this purpose.

The dependent claims and the following description in each case contain particularly advantageous embodiments and developments of the invention. In particular, the claims of one claim category can also be developed analogously to the dependent claims of a different claim category. Within the context of the invention, the various features of different exemplary embodiments and claims can also be combined to yield new exemplary embodiments.

In one embodiment of the method according to the invention for generating a combined contrast medium and blood vessel representation of breast tissue to be examined, a synthesis image data set is ascertained on the basis of one of the two projection measurement data sets. The synthesis image data set includes a tomosynthesis image data set or alternatively a synthetic mammogram. Subsequently, the blood vessel image is ascertained on the basis of the ascertained synthesis image data set. A tomosynthesis image data set advantageously includes information on projections from various angles, with the result that a synthetic three-dimensional image can be reconstructed. It is possible in this manner to visualize blood vessel structures that would cover each other in a simple projection and therefore would, at least in part, not be detectable.

The blood vessel image that is ascertained during the method according to the invention for generating a combined contrast medium and blood vessel representation of breast tissue to be examined can be ascertained, for example, from a combination of the two first and second image data sets. It is possible in this way to combine information of image representations with various contrasts for the blood vessel representation.

The dual-energy image data set that is ascertained during the method according to the invention for generating a combined contrast medium and blood vessel representation of breast tissue to be examined can include, for example, a two-dimensional image data set or a three-dimensional image data set. A three-dimensional representation has the advantage that image information for all three dimensions of a region to be examined is available. For example, in a breast examination, covering of relevant regions in the image representation is prevented. The dual-energy image data set preferably includes a dual-energy mammogram. A mammogram representation is typically a two-dimensional representation of the breast that corresponds to a standard representation and can be easily processed by the diagnostics personnel.

The dual-energy image data can be generated, for example, with the aid of a subtraction of weighted image intensities of the two image data sets. The image intensities or intensities of the individual image pixels of the two image data sets are preferably weighted in such a way that background structures disappear in the subtraction of the intensity values of the image data. What is achieved in this way is a significantly better ability to find lesions, which can be connected, for example, to tumors. The weighting is dependent on the compression thickness and the tissue thickness of the breast to be examined.

In one embodiment of the method according to the invention for generating a combined contrast medium and blood vessel representation of breast tissue to be examined, the first and second x-ray projection measurement data are obtained with the aid of a CT imaging method. It is possible by using a CT imaging method to generate highly resolved three-dimensional image representations, which can also be represented, for example, in the form of a plurality of slice images and can be used both as an overall image and as so-called slice images for the diagnosis.

In one particularly preferred variant of the method according to the invention for generating a combined contrast medium and blood vessel representation of breast tissue to be examined, ascertainment of the blood vessel image is effected with the aid of a multiscaling blood vessel thickening on the basis of the Frangi method in at least one of the two image data sets. The Frangi method is described in A. F. Frangi, et al., "Multiscale Vessel Enhancement Filtering" in Medical Image Computing and Computer-Assisted Intervention—MICCAI'98, W. M. Wells, A. Colchester and S. L. Delp (eds.), Lecture Notes in Computer Science, vol. 1496—Springer Verlag, Berlin, Germany, pp. 130-137. Proportions that disturb the blood vessel representation in an image representation are suppressed or reduced with the aid of the Frangi method, with the result that the vessels are more clearly discernible.

Alternatively, ascertainment of the blood vessel image can be effected with the aid of a preferably automatic segmentation of the breast vessels in at least one of the two image data sets. Such a method is likewise illustrated in Frangi, et al. Further information relating to this method can be found in Staring, et al. "Pulmonary Vessel Segmentation using Vessel Enhancement Filters."

In one preferred embodiment of the method according to the invention for generating a combined contrast medium and blood vessel representation of breast tissue to be examined, the illustration of blood vessels is effected in the blood vessel image in dependence on a threshold value. In this case, only vessels having an assigned image signal or signal-to-noise ratio of the image signal which is above the threshold value are represented. Preferably, the threshold value is ascertained from clinical data or is alternatively parameterizable. In this special embodiment, only blood vessels having a specific minimum contrast are taken into account to simplify the representation and enhance its clarity.

The representation of the blood vessel image together with the dual-energy image data set can be effected sequentially or simultaneously. Sequential representation permits viewing of the complete image information of the two partial representations. On the other hand, simultaneous representation permits easy local assignment of image information of the two different image data sets. As part of the simultaneous representation, the ascertained blood vessel image can be merged with the dual-energy image data set to form one superposition image in which both the structures that are highlighted by the contrast medium accumulation and the vessel structures are visible.

In one embodiment of the method according to the invention, the first x-ray energy has an energy value that is below the energy value of the x-ray absorption edge of a contrast medium used for contrast enhancement, and the second x-ray energy has an energy value that is above the energy value of the x-ray absorption edge of the contrast medium used for contrast enhancement. Alternatively, both energy values of the first and the second x-ray energy can be above the energy value of the x-ray absorption edge of the contrast medium used for contrast enhancement, with the first of the two energy values having a low-energy value, i.e. an energy value which is near the energy value of the x-ray absorption edge, and the second energy value including a high-energy value, i.e. which is remote from the energy value of the x-ray absorption edge, with the result that in the case of an image recording with the first energy, contrast-enhanced imaging is effected, and in the case of an image recording with the second energy, non-contrast-enhanced imaging is effected.

As already mentioned, high-energy is understood to mean an energy value that is significantly above an energy value of the absorption edge, in particular of the K-absorption edge, of the contrast medium used. A low energy, in turn, is intended to be understood to mean an energy value that is below or near an energy value of the x-ray absorption edge, in particular the K-absorption edge of the contrast medium used. A low-energy recording in this context is understood to mean a standard energy recording with which a mammogram is typically taken. Energies for such a recording are typically 23 keV to 35 keV.

When generating a superposition image, the weighting of the components of the superposition image is preferably parameterized. For example, parameterization can be individually matched to specific requirements by the operating personnel.

In addition, the merged superposition image can be color-coded. Color coding in an image representation permits the representation of an additional dimension to the graphical representation, which dimension represents additional spatially dependent properties of the represented structures.

In one particularly illustrative embodiment of the method according to the invention for generating a combined contrast medium and blood vessel representation of breast tissue to be examined, regions that are assigned different signal strength threshold values are represented in the blood vessel image in different colors. It is possible in this way to create a type of map with which different vessel concentrations can be visualized in the image.

Other features which are considered as characteristic for the invention are set forth in the appended claims.

Although the invention is illustrated and described herein as embodied in a method and an image data system for generating a combined contrast medium and blood vessel representation of breast tissue to be examined, a computer program product and a computer-readable medium, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL
VIEWS OF THE DRAWING

DETAILED DESCRIPTION OF THE INVENTION

Figure 1:
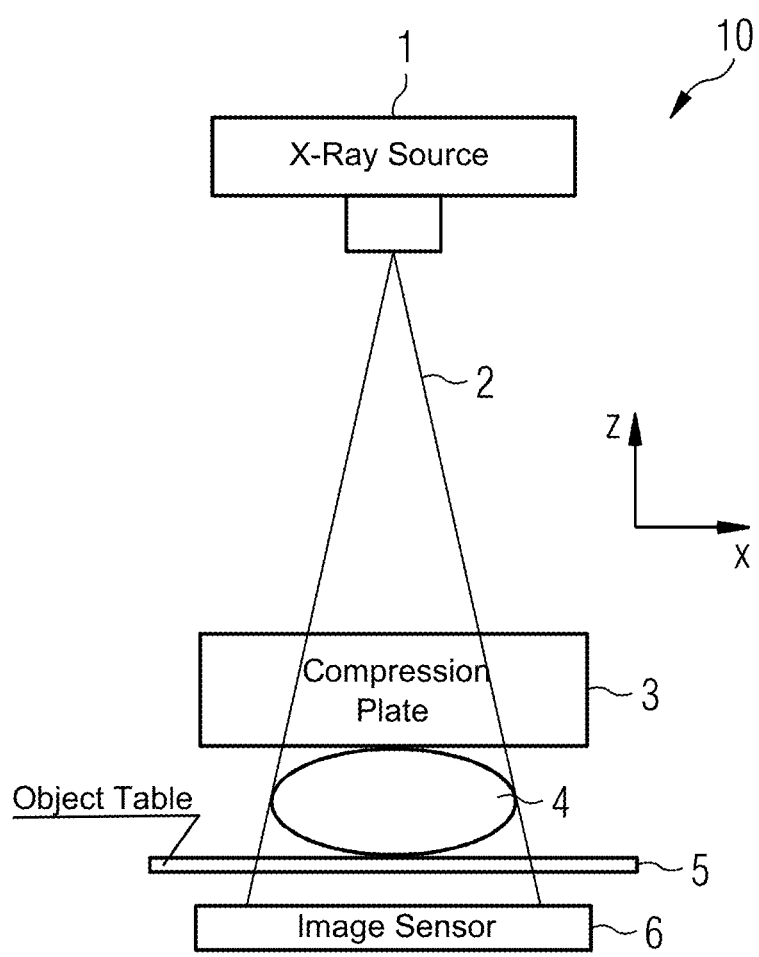
FIG. 1 is a block diagram of a conventional mammography system for two-dimensional x-ray recording of a breast.

Referring now to the figures of the drawings in detail and first, particularly, to FIG. 1 thereof, there is seen a system 10 for two-dimensional x-ray imaging of the breast, which is also referred to as a mammography system. The mammography system 10 includes an x-ray source 1, from which x-rays 2 are emitted in the direction of a breast 4 in the shape or manner of a fan, i.e. a beam that widens orthogonally to the propagation direction. The breast 4 is placed on an object table 5 and is pressed against the object table 5 by a compression plate 3. In this way, the thickness of the breast in the propagation direction of the x-rays, i.e. in the z-direction, is reduced. The reduction of the thickness of the object that is x-rayed is accompanied by a reduction in the scatter radiation. Some of the x-rays that are incident on the breast 4 are absorbed. The remaining x-rays that are incident on the breast 4 are transmitted and captured by an image sensor 6.

Figure 2:
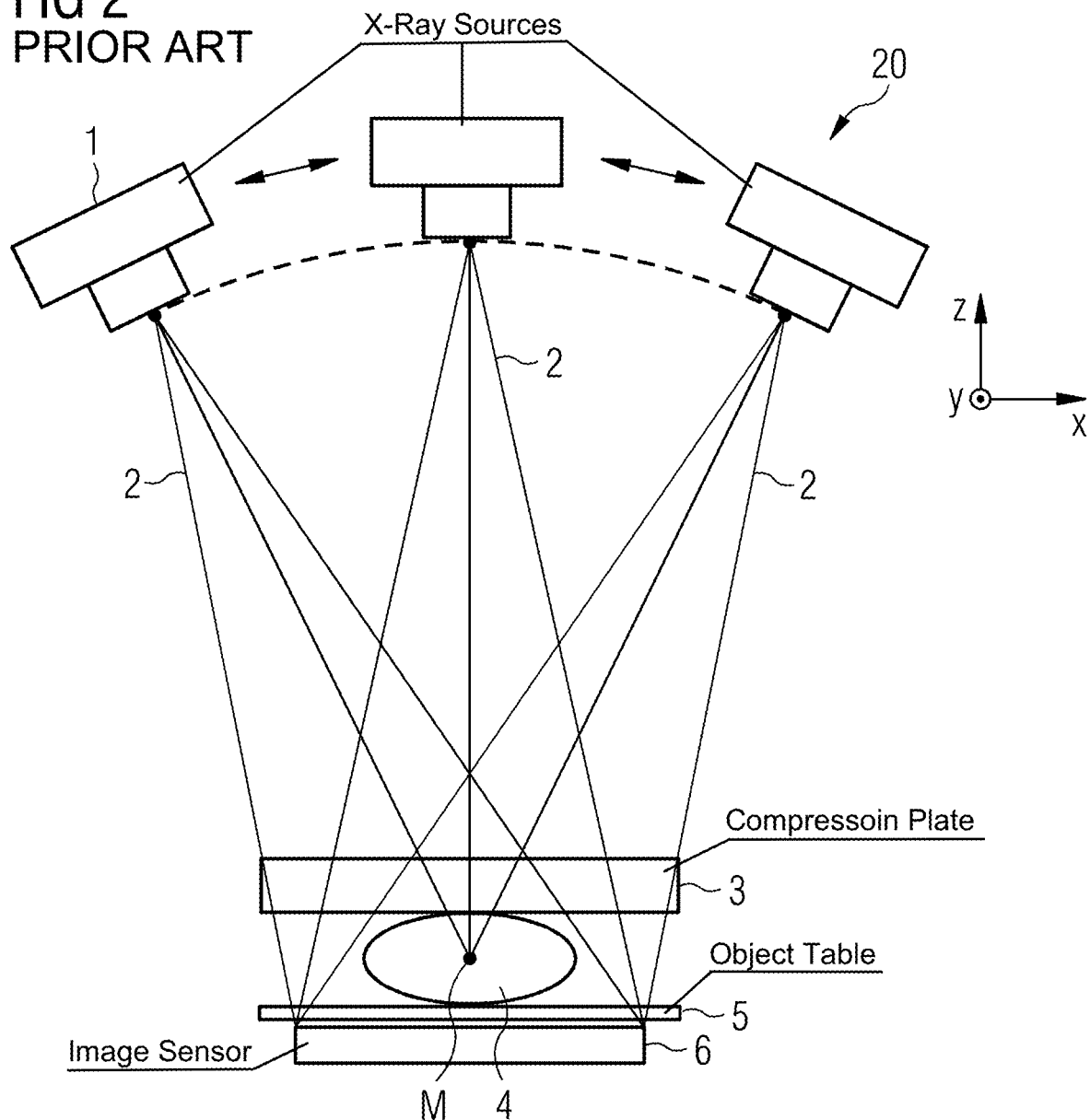
FIG. 2 is a block diagram of a conventional tomosynthesis system for three-dimensional x-ray recording of a breast.

FIG. 2 shows a conventional tomosynthesis system 20 for three-dimensional image recording of a breast 4. Unlike the 2D mammography system 10 shown in FIG. 1, the tomosynthesis system 20 includes an x-ray source 1 that is rotatable about an object center point M and with which x-ray image recordings can be taken of the breast 4 from different directions or angles. The tomosynthesis system 20 shown in FIG. 2 also includes a compression plate 3 that presses the breast 4 to be examined against an object table 5. The breast 4 to be examined is irradiated by the x-ray source 1 from various angles, so that a multiplicity of individual images of the breast 4 are captured by an x-ray detector 6. A three-dimensional layer image is calculated from the individual images, which permits a layer-wise examination of the tissue of the breast 4.

Figure 3:
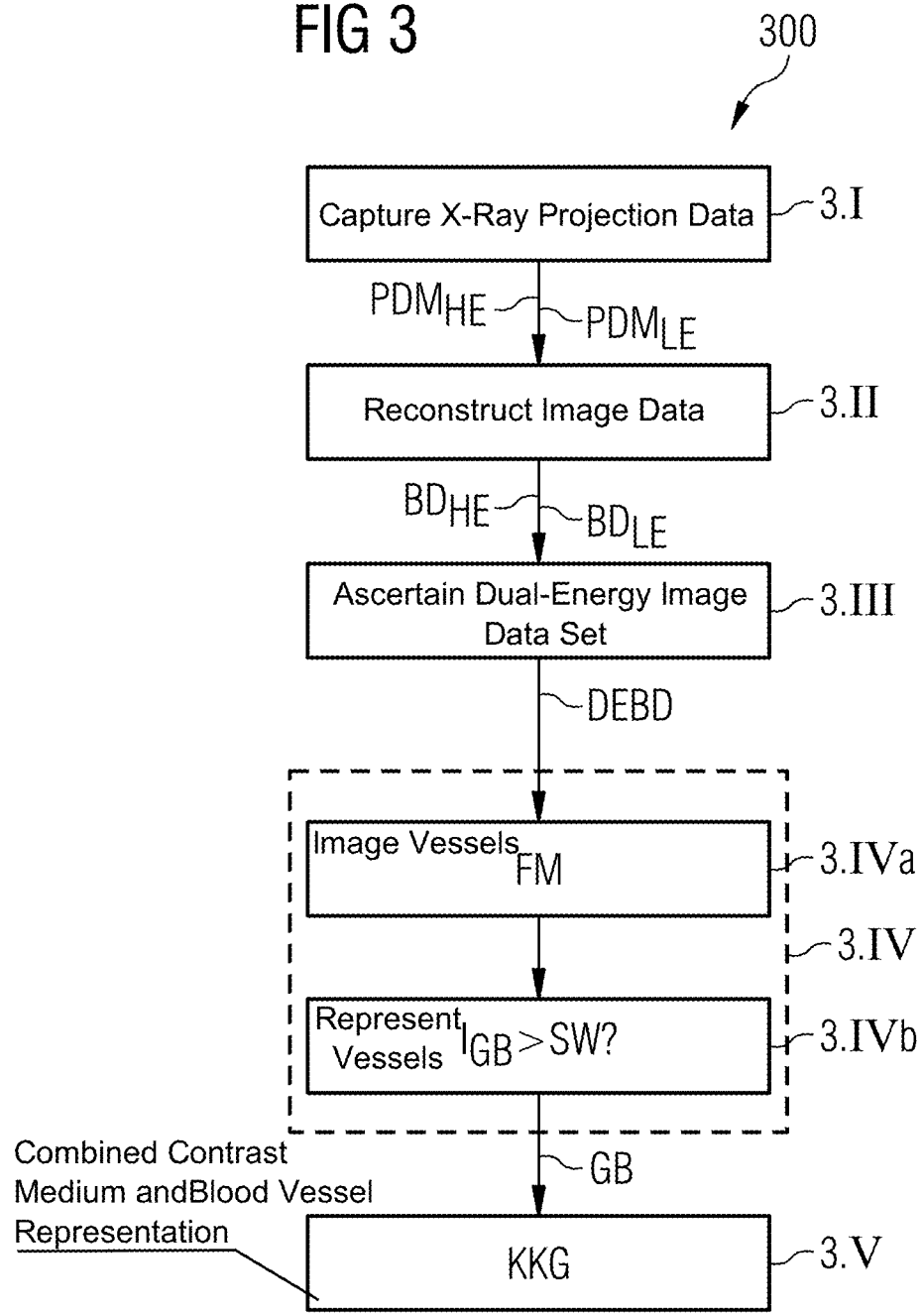
FIG. 3 shows a flowchart, which illustrates a method for generating a combined contrast medium and blood vessel representation of breast tissue to be examined according to one exemplary embodiment of the invention.

FIG. 3 shows a flowchart 300, with which a method for generating a combined contrast medium and blood vessel representation KKG of breast tissue 4 to be examined is illustrated. Prior to the imaging method, a contrast medium is typically injected into the bloodstream of the patient. The contrast medium also reaches the breast through the blood vessels. Blood vessels are located in the breast primarily where lesions are present. In a step 3.I, first x-ray projection measurement data $PMD_{LE}$ of the breast tissue to be examined are captured with a lower x-ray energy $E_L$, i.e. with an x-ray energy that is within the range of the absorption edge for x-rays of the contrast medium. In the step 3.I, second x-ray projection data $PMD_{HE}$ are furthermore captured with a higher x-ray energy $E_H$, i.e. with an x-ray energy having an energy value which is far above the energy value of the absorption edge for x-rays of the contrast medium.

In a step 3.II, first and second image data $BD_{LE}$, $BD_{HE}$ are reconstructed from the captured x-ray projection measurement data $PMD_{LE}$, $PMD_{HE}$. In a step 3.III, a dual-energy image data set DEBD is then ascertained on the basis of the first and second image data $BD_{LE}$, $BD_{HE}$. For example, image intensities $I_{DEBD}$ of the dual-energy image data set DEBD are ascertained as follows:

$$I_{DEBD} = \ln(I_{BDHE}) - w \ast \ln(I_{BDLE}), \quad (1)$$

wherein w is the weighting of the image intensities in dependence on the thickness and the type of the tissue to be examined, $I_{BDLE}$, $I_{BDHE}$ include the image intensities of the first and second image data sets $BD_{LE}$, $BD_{HE}$, and $I_{DEBD}$ represents the image intensity of the dual-energy image data set. The ascertained dual-energy image DEBD forms the regions of the breast tissue to be examined which are more noticeable due to the contrast medium and in which lesions occur. In order to be able to additionally represent the blood vessel structures of the breast tissue, a blood vessel image GB is generated in a step 3.IV on the basis of one of the two image data sets, in this case the first image data set $BD_{LE}$. Imaging of the vessels is effected by a multiscaling vessel thickening based on the Frangi method FM in a step 3.IVa and a subsequent representation of vessels generated in a step 3.IVb, the image intensity $I_{GB}$ of which is above a predetermined threshold value SW. In a step 3.V, the ascertained image data, i.e. the dual-energy image data set DEBD and the blood vessel image GB, are finally graphically represented simultaneously on a screen and made available for breast cancer diagnosis. In the exemplary embodiment described with regard to in FIG. 3, the image data sets DEBD, GB are superpositioned to form the combined image KKG.

Figure 4:
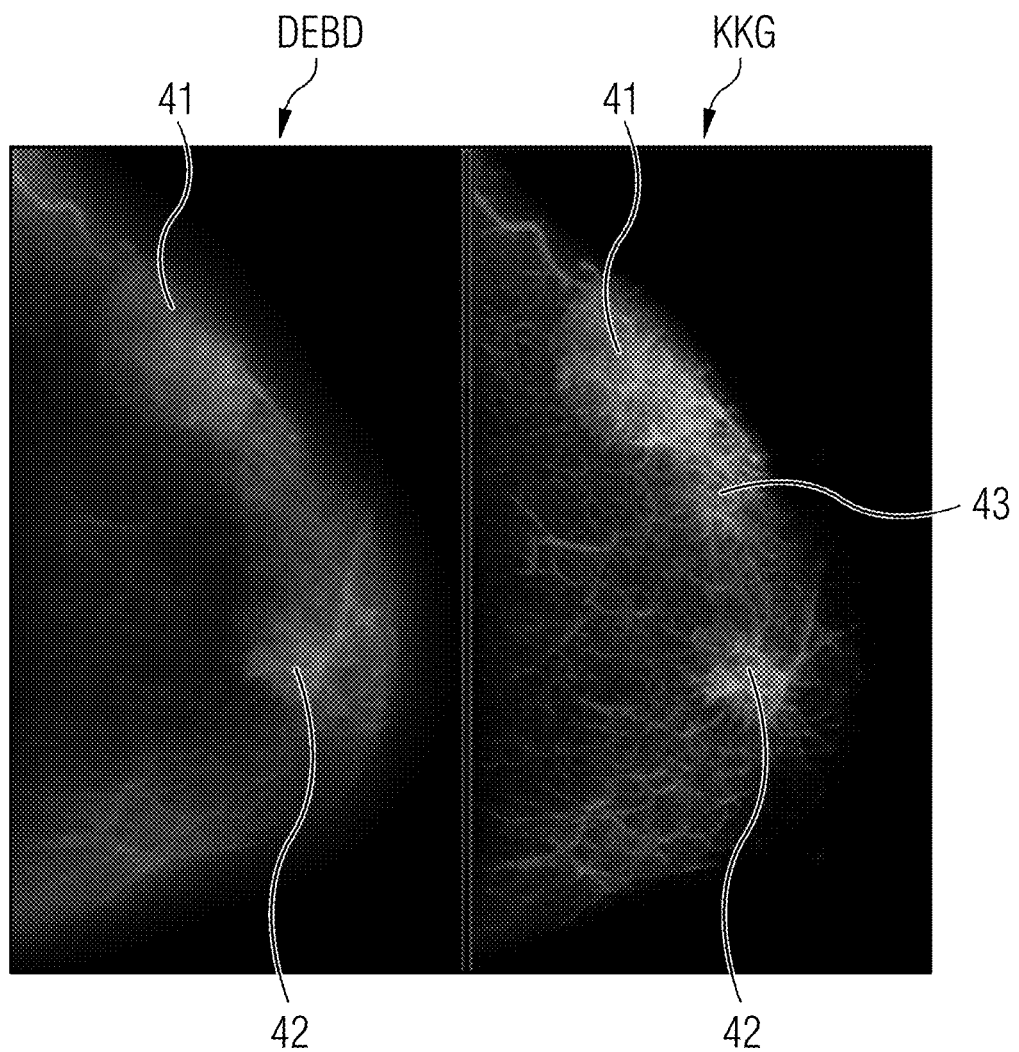
FIG. 4 is a contrast image representation as compared to a combined contrast and blood vessel representation.

FIG. 4 illustrates, in a left-hand partial image, the representation of a dual-energy image DEBD that was generated after administration of an iodine contrast medium. In the left-hand partial image, lesions 41, 42 can be seen. Furthermore, a right-hand partial image in FIG. 4 shows an exemplary representation of a merged image KKG from a dual-energy image DEBD, which was generated after administration of an iodine contrast medium, and a blood vessel image GB. In the right-hand image, in addition to the lesions 41, 42, blood vessels 43 can be seen, which cannot be seen in the left-hand partial image.

Figure 5:
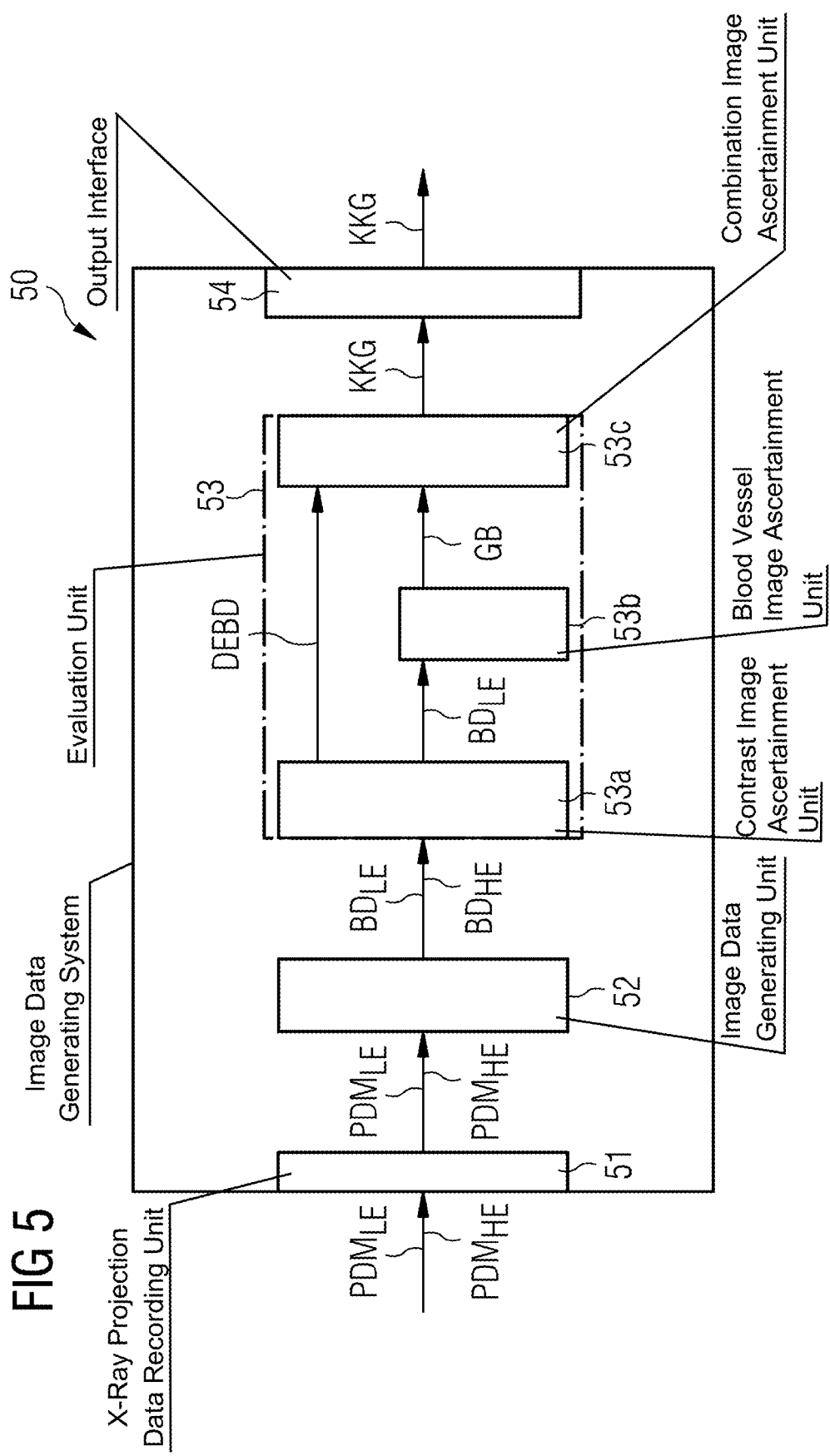
FIG. 5 is a block diagram, with which an image data generating system according to one exemplary embodiment of the invention is represented.

FIG. 5 schematically represents an image data generating system 50 according to one exemplary embodiment of the invention. An x-ray projection data recording unit 51 is part of the image data generating system 50. The x-ray projection data recording unit 51 includes functional units, which permit the acquisition of first and second projection measurement data $PMD_{LE}$, $PMD_{HE}$, which were generated with x-rays with different energy spectra. These functional units can also include, for example, a mammography system 10 or a tomosynthesis system 20, as illustrated in FIG. 1 and FIG. 2, or another imaging system, such as for example a CT system.

The projection measurement data $PMD_{LE}$, $PMD_{HE}$ that were captured by the x-ray projection data recording unit 51 are transmitted to an image data generating unit 52. The image data generating unit 52 generates first and second image data sets $BD_{LE}$, $BD_{HE}$ on the basis of the captured first and second x-ray projection data $PMD_{LE}$, $PMD_{HE}$. The generated image data sets are subsequently transmitted to an evaluation unit 53. The evaluation unit 53 includes a contrast image ascertainment unit 53a, which generates a dual-energy contrast image DEBD on the basis of the image data sets $BD_{LE}$, $BD_{HE}$ that were recorded with different x-ray energies. The evaluation unit 53 additionally has a blood vessel image ascertainment unit 53b. The blood vessel image ascertainment unit 53b likewise contains at least one of the first and second image data sets $BD_{LE}$, $BD_{HE}$, in this case the low-energy image data set $BD_{LE}$. The blood vessel image ascertainment unit 53b generates a blood vessel image GB on the basis of the low-energy image data set $BD_{LE}$. The evaluation unit 53 additionally includes a combination image ascertainment unit 53c. The combination image ascertainment unit 53c receives the reconstructed dual-energy contrast image data DEBD from the contrast image ascertainment unit 53a and receives the blood vessel image data GB that are generated by the blood vessel image ascertainment unit 53b from the latter. The combination image ascertainment unit 53c generates a combined contrast/blood vessel representation KKG of a breast region to be examined on the basis of the received image data DEBD, GB. The ascertained data for the contrast/blood vessel representation KKG are subsequently transmitted to an image representation unit (not shown) through an output interface 54 of the image data generating system 50. The image representation unit can include, for example, a screen unit on which the combined contrast/blood vessel representation KKG is imaged.

In closing, it is pointed out once again that the previously described methods and apparatuses are merely preferred exemplary embodiments of the invention and that the invention can be varied by a person skilled in the art without departing from the scope of the invention to the extent to which it is defined by the claims. The method according to the invention was described in connection with the recording of a two-dimensional mammogram and the recording of a three-dimensional tomosynthesis image. However, the invention also includes image representation with the aid of different imaging methods, such as for example computer tomography. In connection with the use of x-rays with high-energy and low-energy, the terms "high" and "low" are to be understood as being relative to the energy of the x-ray absorption edge of a previously administered contrast medium. For the sake of completeness, it is also pointed out that the use of indefinite articles "a" or "an" does not rule out that the features in question can also be presented multiple times. Likewise, the term "unit" does not rule out that the latter includes several components which can, if appropriate, also be distributed in terms of space.

The invention claimed is:

1. A method for generating a combined contrast medium and blood vessel representation of breast tissue to be examined, the method comprising the following steps:
   capturing first contrast-medium-influenced x-ray projection measurement data with a first x-ray energy and second contrast-medium-influenced x-ray projection measurement data with a second x-ray energy differing from the first x-ray energy;
   reconstructing a first image data set based on the captured first x-ray projection measurement data and a second image data set based on the captured second x-ray projection measurement data;
   ascertaining a dual-energy image data set based on the first and second image data sets;
   ascertaining a blood vessel image based on at least one of the first or second image data sets;
   representing the blood vessel image together with the dual-energy image data set in a combined contrast medium and blood vessel representation; and
   carrying out the representation step by at least one of:
      representing the blood vessel image together with the dual-energy image data set sequentially or simultaneously, or
      merging the ascertained blood vessel image with the dual-energy image data set to form a superposition image in which structures being highlighted due to contrast medium accumulation and blood vessel structures are visible.

2. The method according to claim 1, which further comprises:
   ascertaining a synthesis image data set, including a tomosynthesis image data set or a synthetic mammogram, based on one of the first or second projection measurement data; and
   ascertaining the blood vessel image based on the ascertained synthesis image data set.

3. The method according to claim 1, which further comprises ascertaining the blood vessel image from a combination of the first and second image data sets.

4. The method according to claim 1, wherein the dual-energy image data set includes a two-dimensional image data set or a three-dimensional image data set or a dual-energy mammogram.

5. The method according to claim 1, which further comprises obtaining the first and second x-ray projection measurement data by using a CT imaging method.

6. The method according to claim 1, which further comprises ascertaining the blood vessel image by using multi-scaling blood vessel thickening based on the Frangi method, or by using a segmentation of breast vessels in at least one of the first or second image data sets.

7. The method according to claim 6, wherein the segmentation of breast vessels is automatic.

8. The method according to claim 1, which further comprises representing blood vessels in the blood vessel image in dependence on a threshold value, and representing only vessels having an assigned image signal or a signal to noise ratio of the image signal above the threshold value.

9. The method according to claim 8, wherein the threshold value is ascertained from clinical data or is parameterizable.

10. The method according to claim 1, wherein:
    the first x-ray energy has a first energy value below an energy value of an x-ray absorption edge of a contrast medium used for contrast enhancement, or
    the second x-ray energy has a second energy value above an energy value of an x-ray absorption edge of the contrast medium used for contrast enhancement, or
    both energy values of the first and second x-ray energies are above the energy value of the x-ray absorption edge of the contrast medium used for contrast enhancement, and
    the first energy value is relatively near the energy value of the x-ray absorption edge and the second energy value is relatively remote from the energy value of the x-ray absorption edge, providing contrast-enhanced imaging in an image recording with the first energy, and providing non-contrast-enhanced imaging in an image recording with the second energy.

11. The method according to claim 1, wherein the superposition image has components with a weighting being parameterizable.

12. The method according to claim 1, wherein the merged superposition image is color-coded.

13. The method according to claim 12, which further comprises representing regions being assigned different signal strength threshold values in the blood vessel image in different colors.

14. A non-transitory computer program product having a computer program, which is loadable directly into a storage unit of an image data generating system, with control sections for carrying out all of the steps of the method according to claim 1 when the computer program is executed in the image data generating system.

15. A non-transitory computer-readable medium, on which control sections which are readable and executable by a computer unit of an image data generating system are stored to carry out all of the steps of the method according to claim 1 when the control sections are executed by the computer unit of the image data generating system.

16. An image data generating system, comprising:
a projection data capturing unit for capturing first contrast-medium-influenced x-ray projection measurement data with a first x-ray energy and second contrast-medium-influenced x-ray projection measurement data with a second x-ray energy differing from the first x-ray energy;
an image data generating unit for reconstructing a first image data set of breast tissue to be examined based on the captured first x-ray projection measurement data and a second image data set of the breast tissue to be examined based on the captured second x-ray projection measurement data; and
an evaluation unit including:
a dual-energy image ascertainment unit configured to ascertain a dual-energy image data set based on the first and the second image data sets,
a blood vessel image ascertainment unit configured to ascertain a blood vessel image based on at least one of the first or second image data sets, and
a combination image ascertainment unit configured to ascertain a combined contrast medium and blood vessel representation of the blood vessel image and of the dual-energy image data set;
the combination image ascertainment unit being configured to ascertain the combined contrast medium and blood vessel representation by at least:
representing the blood vessel image together with the dual-energy image data set sequentially or simultaneously; or
merging the ascertained blood vessel image with the dual-energy image data set to form a superposition image in which structures being highlighted due to contrast medium accumulation and blood vessel structures are visible.

* * * * *